US012648612B1

(12) United States Patent
Chen et al.

(10) Patent No.: US 12,648,612 B1
(45) Date of Patent: Jun. 9, 2026

(54) MECHANICAL SUPPORT DEVICE COMPRISING A VARIABLE IMPEDANCE MODULE

(71) Applicant: Human Motion Technologies LLC, Pittsburgh, PA (US)

(72) Inventors: Tianyao Chen, Pittsburgh, PA (US); Joshua M. Caputo, Pittsburgh, PA (US)

(73) Assignee: Human Motion Technologies LLC, Pittsburgh, PA (US)

( * ) Notice: Subject to any disclaimer, the term of this patent is extended or adjusted under 35 U.S.C. 154(b) by 180 days.

(21) Appl. No.: 18/243,960

(22) Filed: Sep. 8, 2023

Related U.S. Application Data

(60) Provisional application No. 63/404,716, filed on Sep. 8, 2022.

(51) Int. Cl.
*A43B 7/20* (2006.01)
*A61F 2/50* (2006.01)
*A61F 2/66* (2006.01)

(52) U.S. Cl.
CPC .............. *A43B 7/20* (2013.01); *A61F 2/6607* (2013.01); *A61F 2002/5006* (2013.01)

(58) Field of Classification Search
CPC ........ A43B 7/20; A61F 5/0111; A61F 5/0113; A61F 5/0127; A61F 2005/0169; A61F 2005/0179; A61F 2/6607; A61F 2002/5006
See application file for complete search history.

(56) References Cited

U.S. PATENT DOCUMENTS

| | | | | |
|---|---|---|---|---|
| 827,720 | A * | 8/1906 | Erwin ................... | A61F 2/6607 |
| | | | | 623/49 |
| 5,891,061 | A * | 4/1999 | Kaiser ................... | A61F 5/0125 |
| | | | | 601/33 |
| 2018/0104083 | A1* | 4/2018 | Lee ........................ | A61F 5/0127 |

FOREIGN PATENT DOCUMENTS

EP 3613389 A1 * 2/2020 ........... A61F 2/6607

* cited by examiner

*Primary Examiner* — Kari K Rodriquez
(74) *Attorney, Agent, or Firm* — K&L Gates LLP

(57) ABSTRACT

A mechanical support device comprising a variable impedance module is disclosed herein. The variable impedance module is configured to adjustably control a stiffness, a damping, and/or a range of motion of a joint. In various instances, the mechanical support device is intended for use with an ankle joint. In such instances, the mechanical support device further comprises a shoe and an ankle brace releasably coupled to the shoe.

13 Claims, 7 Drawing Sheets

100
200
150

100
200'
150

100
200"
150

| Property | Value (or value range) |
|---|---|
| RoM | $-30^0$ (dorsi) to $35^0$ (plantar) |
| Max stiffness | 1 Nm/deg |
| Hardstop stiffness | 11.5 Nm/deg |
| Max torque | 80 Nm |
| Weight | 1.6 kg (with sneaker) |

FIG. 6

MECHANICAL SUPPORT DEVICE COMPRISING A VARIABLE IMPEDANCE MODULE

CROSS-REFERENCE TO RELATED APPLICATION

The present application claims priority under 35 U.S.C. § 119(e) to U.S. Provisional Patent Application Ser. No. 63/404,716, titled MECHANICAL SUPPORT DEVICE COMPRISING A VARIABLE IMPEDANCE MODULE, filed Sep. 8, 2022, the disclosure of which is herein incorporated by reference in its entirety.

STATEMENT REGARDING FEDERALLY SPONSORED RESEARCH OR DEVELOPMENT

This invention was made with government support under W81XWH-20-P-0052 awarded by the Defense Health Agency, Medical Research and Development Branch. The government has certain rights in the invention.

BACKGROUND

Tendon injuries in the lower extremities can significantly impact activity levels and quality of life. Achilles, patellar, and quadriceps tendon tears, as well as plantar fasciitis, are common in United States (US) military personnel, athletes, and other highly-active populations. The lesions of the Achilles tendon are termed chronic if they are left untreated for more than 4 weeks. Acute Achilles injuries and ruptures that are not properly rehabilitated often lead to chronic Achilles tendinopathy. Earlier rehabilitative intervention is shown to improve outcomes for this type of ankle injury.

Typical treatment of ankle injuries includes the use of plaster casts and functional bracing. Increasingly prevalent evidence suggests that traditional plaster casts do not perform better than functional bracing. Moreover, functional bracing has been found to be preferred by patients to cast immobilization and is associated with better outcomes. Improved biomechanical outcomes, such as increased dorsiflexion, and an earlier return to activity have been demonstrated for patients who bear weight in a walking boot early in the recovery process. Introducing newer, more effective technology for a large population who are receptive to functional bracing will have a powerful impact on a wide range of end-users.

Passively actuated devices are likely to benefit larger populations due to their relatively low cost, great robustness, and lower regulatory and reimbursement barriers as compared to powered and/or microprocessor controlled technologies.

SUMMARY

Various mechanical support devices are disclosed herein. The mechanical support device can enable a wearer with a musculoskeletal injury to move and/or operate safely during recovery. The mechanical support devices comprise a variable impedance module (VIM) to provide for adjustability of stiffness and/or range of motion in a lightweight, compact, and robust package. In various instances, the mechanical support device comprises an exoskeleton, such as an ankle exoskeleton.

The mechanical support devices described herein provide variable stiffness and range of motion. The degree of bracing is adjustable based on an individual's need and/or progression through the rehabilitation process. The adjustability of the mechanical support devices enables the individual and/or a clinician to tune the support of the brace according to a preferred stiffness level and range of motion. The mechanical support devices disclosed herein can replace conventional rehabilitation equipment such as immobilization boots, hinged braces, compressive braces, flexibility bands, TheraBands®, and/or immobilization boards with a single, simple, and highly-adjustable device.

BRIEF DESCRIPTION OF THE DRAWINGS

Various features of the exemplary embodiments described herein, together with advantages thereof, may be understood in accordance with the following description taken in conjunction with the accompanying drawings as follows:

FIG. 6 is a table depicting various specification of the mechanical support device.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Mechanical support devices can enable a wearer with a musculoskeletal injury to move and/or operate safely during recovery. The mechanical support devices described herein comprise a variable impedance module (VIM) to provide for adjustability of stiffness and/or range of motion in a light-weight, compact, and robust package. In various instances, the mechanical support device comprises an exoskeleton, such as an ankle exoskeleton.

The mechanical support devices described herein provide variable stiffness and range of motion. The degree of bracing is adjustable based on an individual's need and/or progression through the rehabilitation process. The adjustability of the mechanical support devices enables the individual and/or a clinician to selectively tune the support of the brace according to a preferred stiffness level and/or range of motion. The mechanical support devices disclosed herein can replace conventional rehabilitation equipment such as immobilization boots, hinged braces, compressive braces, flexibility bands, TheraBands®, and/or immobilization boards with a single, simple, and highly-adjustable device.

Figures 1A, 1B, 1C:
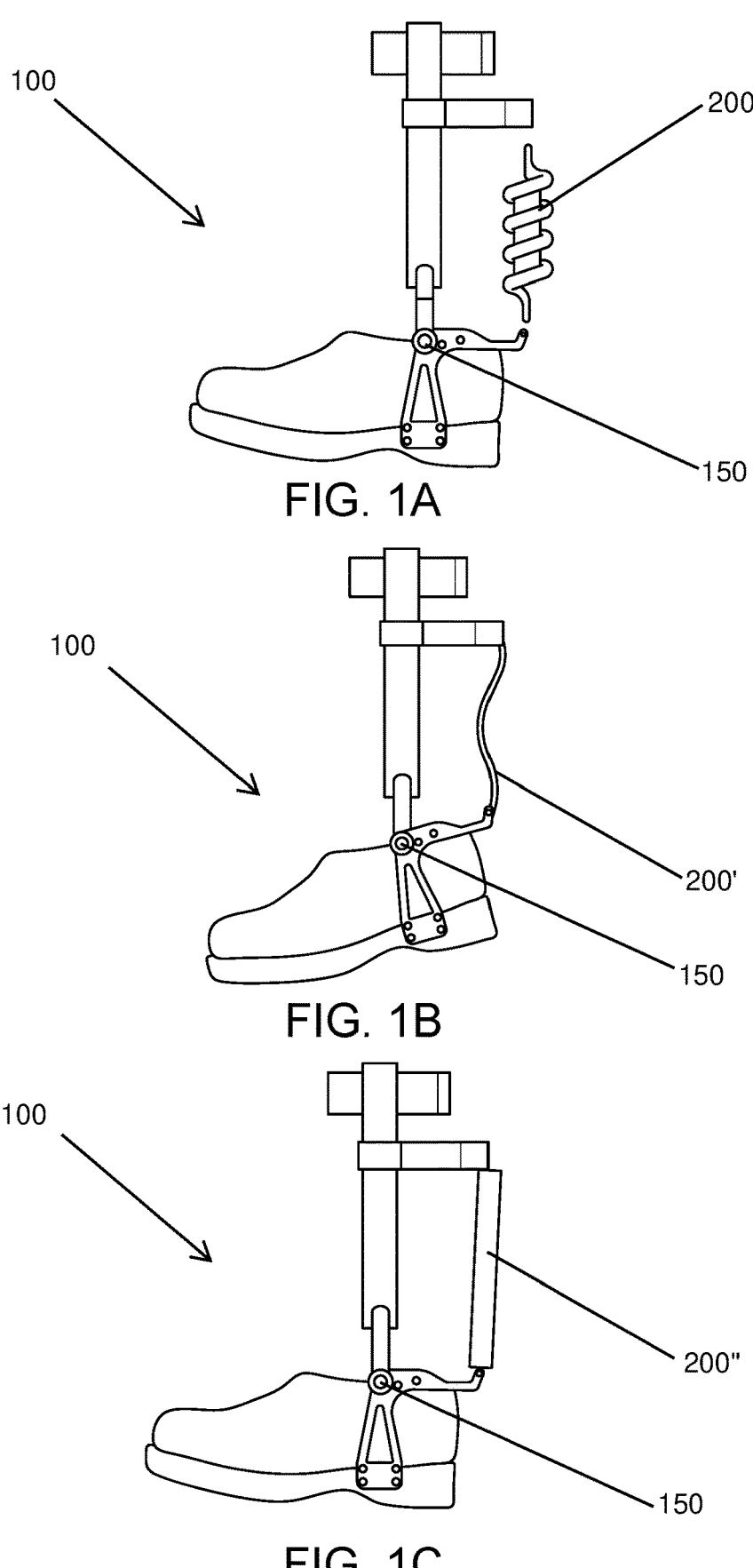
FIG. 1A is an elevation view of a mechanical support device, or exo-brace, comprising a module to provide spring-like resistance to selectively control a range of motion and/or stiffness of a target joint.
FIG. 1B is an elevation view of the mechanical support device of FIG. 1A alternatively, or additionally, providing a rope-like resistance to selectively control a range of motion and/or stiffness of the target joint.
FIG. 1C is an elevation view of the mechanical support device of FIGS. 1A and 1B alternatively, or additionally, immobilizing at least a portion of the target joint.

In various instances, support is provided by a mechanical support device to a person with a musculoskeletal injury to mitigate further injury and/or support recovery. Due to the nature of the injury and/or the progression of recovery, a desired form and/or degree of support provided by the mechanical support device can differ and/or evolve. As depicted in FIGS. 1A-1C a single mechanical support device 100 is able to selectively provide different forms and/or degrees of support to a target joint. More specifically, FIGS. 1A-1C depict a mechanical support device 100, or exo-brace, comprising adjustable ankle joint range of motion and/or stiffness to support an ankle joint of a person. For example, as shown in FIG. 1A, it may be desirable for the mechanical support device to provide a spring-like resistive torque 200 to drive an assisted joint 150 to a neutral position. As shown in FIG. 1B, it may be desirable for the mechanical support device to limit a range of motion of a target joint 150 by constraining movement through a rope-like resistance 200'. As shown in FIG. 1C, it may be for the mechanical support device to immobilize, or otherwise prevent a particular movement, of the joint 150. While such selective movement limitations and/or assistances are shown individually in FIGS. 1A-1C, it is envisioned that the mechanical support device can provide any suitable single movement assistance and/or combination of movement assistances at any given time.

The exo-brace 100 is designed to be highly adjustable such that it can provide wide-ranging mechanical behavior to assist a variety of individuals and/or injury types. The exo-brace 100 comprises a variable impedance module (VIM) 200, 200', 200" to achieve such adjustability to limit a movement of a particular joint. The VIM 200, 200', 200" comprises a device that exerts force determined by geometric constraints. For example, the VIM 200, 200', 200" exerts a force determined by its length and moving speed.

As shown in FIG. 1A, the variable impedance module (VIM) 200 is configured to be spring-like. Stated another way, a resistive torque drives the joint to a neutral position. Represented in FIG. 1B, the VIM 200' is configured to additionally or alternatively limit range of motion of a targeted joint. In such instances, the VIM 200' is configured to be rope-like. For example, an ankle joint can move freely with zero resistance until being met with nearly-rigid resistance. FIG. 1C depicts a mechanical support device 100 comprising a VIM 200" to additionally or alternatively immobilize a particular movement. The structure of the exo-brace 100 mimics an immobilization boot by locking the VIM 200". Such immobilization controls sagittal-plane mechanics while frontal and coronal-plane mechanics remain mildly constrained. Stated another way, when a user is wearing the exo-brace 100 shown in FIG. 1C, the frontal and coronal-plane mechanics are not as free as when the user is wearing normal, street shoes; however, such frontal and coronal-plane mechanics are not as constrained when a user is wearing the exo-brace 100 shown in FIG. 1C as when the user is wearing an immobilization boot. While the depicted mechanical support device 100 is described as controlling sagittal-plane mechanics, various embodiments are envisioned where the mechanical support device has control over any combination of sagittal, frontal, and/or coronal-planes.

FIGS. 2A-2E depict various views of a mechanical support device 300 used to support an ankle joint. The mechanical support device 300 comprises a shoe 310, 310', an ankle brace 320, and a variable impedance module (VIM) 350. As described above with respect to FIGS. 1A-1C, the VIM 350 provides a selective adjustability of stiffness and/or range of motion in a lightweight, compact, and robust package. The mechanical support device 300 is further illustrated as comprising a strap to surround the wearer's calf.

The mechanical support device 300 is designed to interface with a shoe 310, 310' of the user. More specifically, the ankle brace 320 is releasably attached to a midsole 315 of the shoe 310, 310'; however, the mechanical support device 300 is easily integrated into the shoe in any suitable manner. Such modularity allows for the mechanical support device 300 to be easily put on and removed by the user. The mechanical support device 300 can be disassembled from the shoe 310, 310' without compromising the functionalities of the shoe 310, 310'. The mechanical support device 300 applies ankle torque to the user through the shoe 310, 310'.

Figures 2A, 2B, 2C, 2D, 2E:
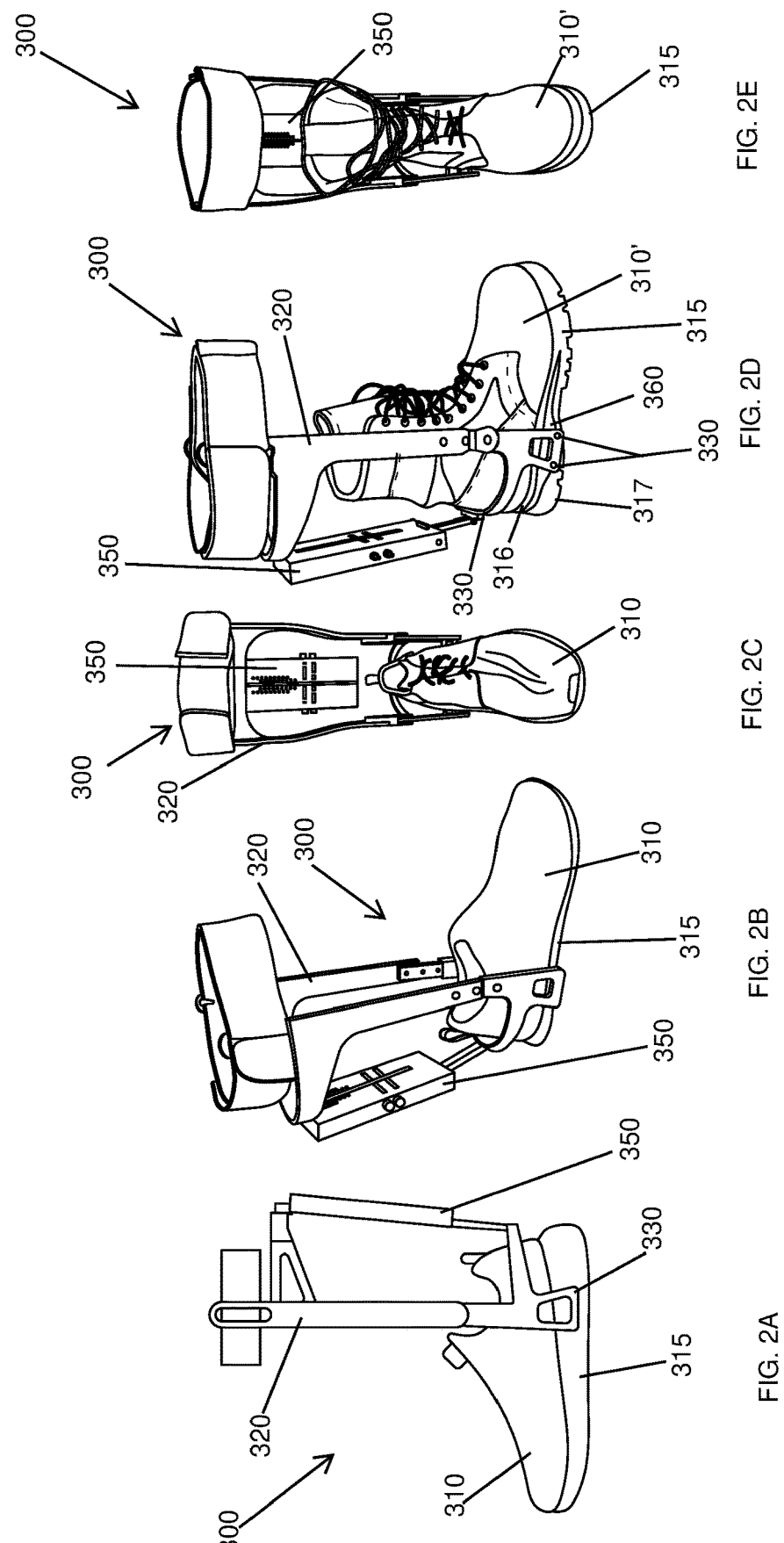
FIG. 2A is an elevation view of a first side of a mechanical support device used to support an ankle joint integrated with a tennis shoe.
FIG. 2B is an elevation view of a second side of the mechanical support device of FIG. 2A.
FIG. 2C is a front view of the mechanical support device of FIGS. 2A and 2B.
FIG. 2D is an elevation view of a side of the mechanical support device of FIG. 2A integrated with a work boot.
FIG. 2E is a front view of the mechanical support device of FIG. 2D.

Although FIGS. 2A-2C depict the mechanical support device 300 being integrated with tennis shoes 310 and FIGS. 2D and 2E depict the mechanical support device 300 integrated with boots 310', any suitable shoe is envisioned for use with the mechanical support device. Moreover, the mechanical support device 300 is compatible with and/or able to be interchangeably used with different shoes and/or types of shoes. In various instances, any high-top, lace-up shoe and/or boot is preferable for use with the mechanical support device. For example, the shoe can be a boot, a running shoe, dress shoes, sandals, and/or sneakers.

As shown in FIG. 2D, a rigid, preferably unhinged, insert 360 can be attached to and/or otherwise incorporated within the sole 315 of the shoe, preferably between an inner layer 316 and an outer layer 317 of the shoe's sole, to create an enforced midsole. In such instances, the rigid insert 360 is inserted into the sole 315 of the shoe 310' without damaging the functionality of the shoe 310' itself. The rigid insert 360 is comprised of any suitable material capable of providing a level of rigidity to the sole of the shoe. In various instances, the rigid insert 360 is comprised of metal, carbon fiber, aluminum, hard plastic, and/or any combination thereof. The rigid insert 360 may extend an entire length of the sole or may extend any suitable length along the sole 315 that is less than the complete length of the sole.

The midsole of the footwear can comprise at least one attachment interface 330 to facilitate releasable coupling to an accessory external device, such as the mechanical support device. The attachment interface 330 of the footwear can be a universal interface for coupling to numerous accessories. In various instances, the footwear comprises an attachment interface 330 on both a lateral side and a medial side of the footwear. In other instances, the attachment interface is present on only one of the lateral or medial sides of the footwear. In various instances, an attachment interface is positioned on a heel of the footwear. However, the footwear can have any suitable location and quantity of attachment interfaces that facilitate a secure connection between the footwear and the mechanical support device. For example, the attachment interface can comprise apertures defined in the midsole that are sized to receive a connection means, such as mounting screws, therein. The mechanical support device comprises a corresponding attachment portion to the attachment interface of the footwear. For example, the attachment portion of the mechanical support device 300 can comprise a mounting bracket with holes and/or apertures defined therein to receive the connection means.

The attachment interface of the footwear and the attachment portion of the mechanical support device can have any features and/or geometry to facilitate a releasable connection therebetween. Similarly, the connection means can comprise any form of fastener that enhance, secure, and/or maintain a suitable connection between the footwear and the mechanical support device while also allowing for the footwear and the mechanical support device to be readily decoupled from one another when desired. Examples of such connection means comprise, pins, screws, bolts, latches, magnets and/or any combination thereof. In various instances, the connection means comprise a threaded, press-fit, and/or friction-fit relationship between the attachment interface and the attachment portion.

Attachment of the ankle brace to the midsole of the shoe ensures the torque is delivered to the wearer of the mechanical support device. The midsole of the shoe is an ideal attachment interface as the midsole is a universal shoe component present in almost all forms of footwear. While the mechanical support device is shown integrated with a tennis shoe and boot, the mechanical support device is compatible and/or intended for use with any suitable form of footwear.

Figures 3A, 3B, 3C:
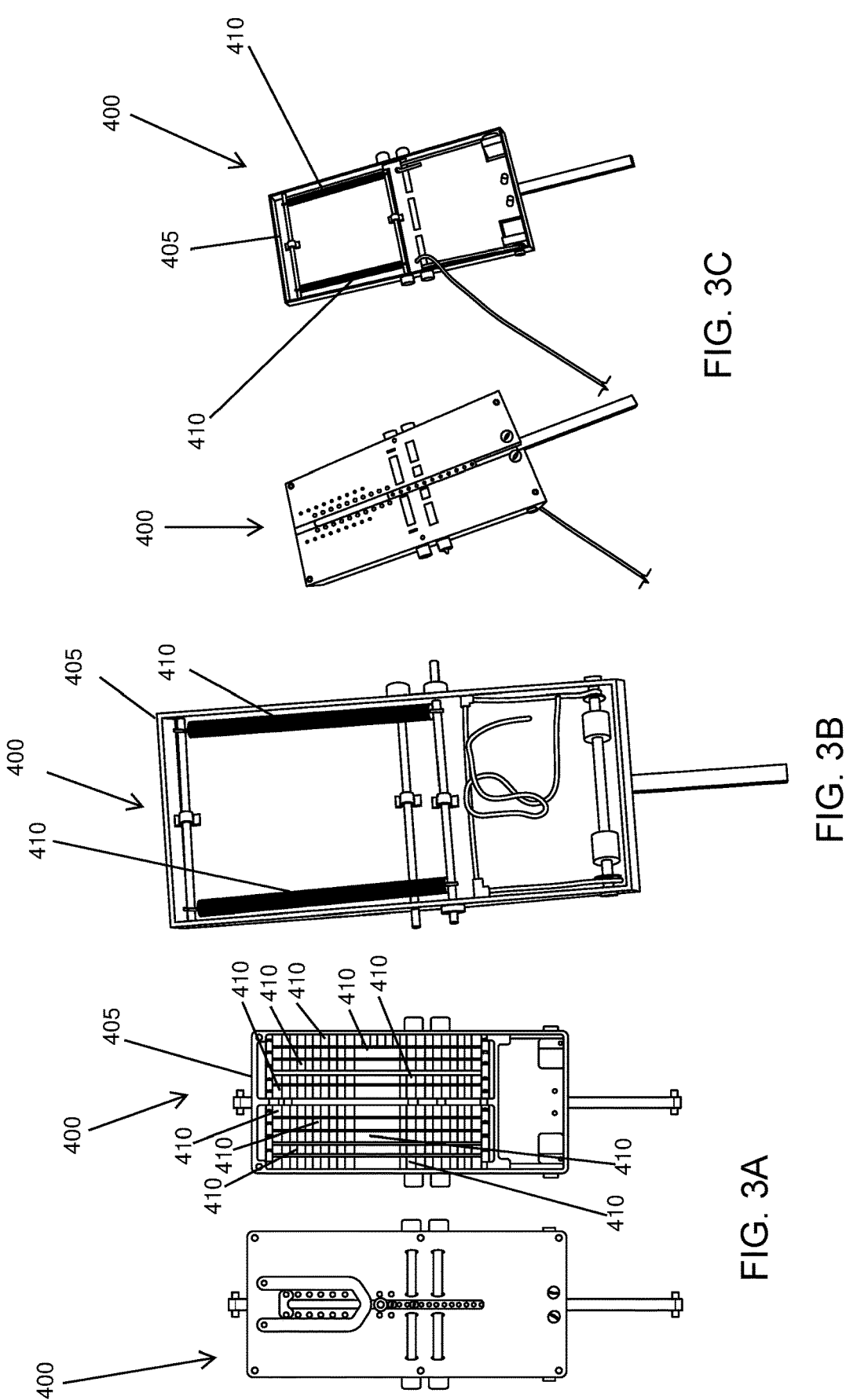
FIG. 3A depicts front and back views of a variable impedance module for use with a mechanical support device.
FIG. 3B is a schematic of a 3D-printed prototype of the variable impedance module of FIG. 3A.
FIG. 3C is depicts front and back views of a prototype of the variable impedance module of FIG. 3A.

An exemplary variable impedance module (VIM) 400, similar to the VIM 200, 200', 200', 350, is depicted in FIGS. 3A-3C. The VIM 400 behaves similar to a variable-stiffness spring with adjustable stops. At the equilibrium position, the VIM 400 exerts no force. When compressed or extended, the VIM 400 generates restoring force which acts to bring a body to its equilibrium position. The adjustability of stiffness is achieved by changing the geometry of the transmission inside the VIM 400. In various instances, the VIM is manufactured out of aluminum, although other suitable material can be used that provides durability and/or protection to the components of the VIM. Stiffness, damping, and range of motion are independently adjustable through the VIM.

FIG. 3A depicts front and back views of the variable impedance module (VIM) 400. FIG. 3B is a schematic of a 3D-printed prototype of the VIM 400, whereas FIG. 4C depicts front and back view of a prototype of the VIM 400. While the prototype shown in FIG. 3C comprises two coil springs 410, a housing 405 of the depicted VIM 400 is sized to fit up to ten coil springs as shown in FIG. 3A. Stated another way, the VIM 400 can comprise any desired number of coil springs that will fit within the housing 405. As the number of coil springs 410 in the VIM 400 increases, the resultant forces increase, for example. The coil spring's power-storing capacity is correlated to its weight and size. The rest length and max length of the coil spring(s) have influence on the achievable range of motion of the mechanical support device. When the spring(s) 410 is compressed, and the length of the coil spring(s) 410 is shorter than its rest length, the VIM 400 produces a pushing force. Conversely, when the spring(s) 410 is stretched, and the length of the coil spring(s) 410 is longer than its rest length, the VIM (400) produces a pulling force.

Figure 4:
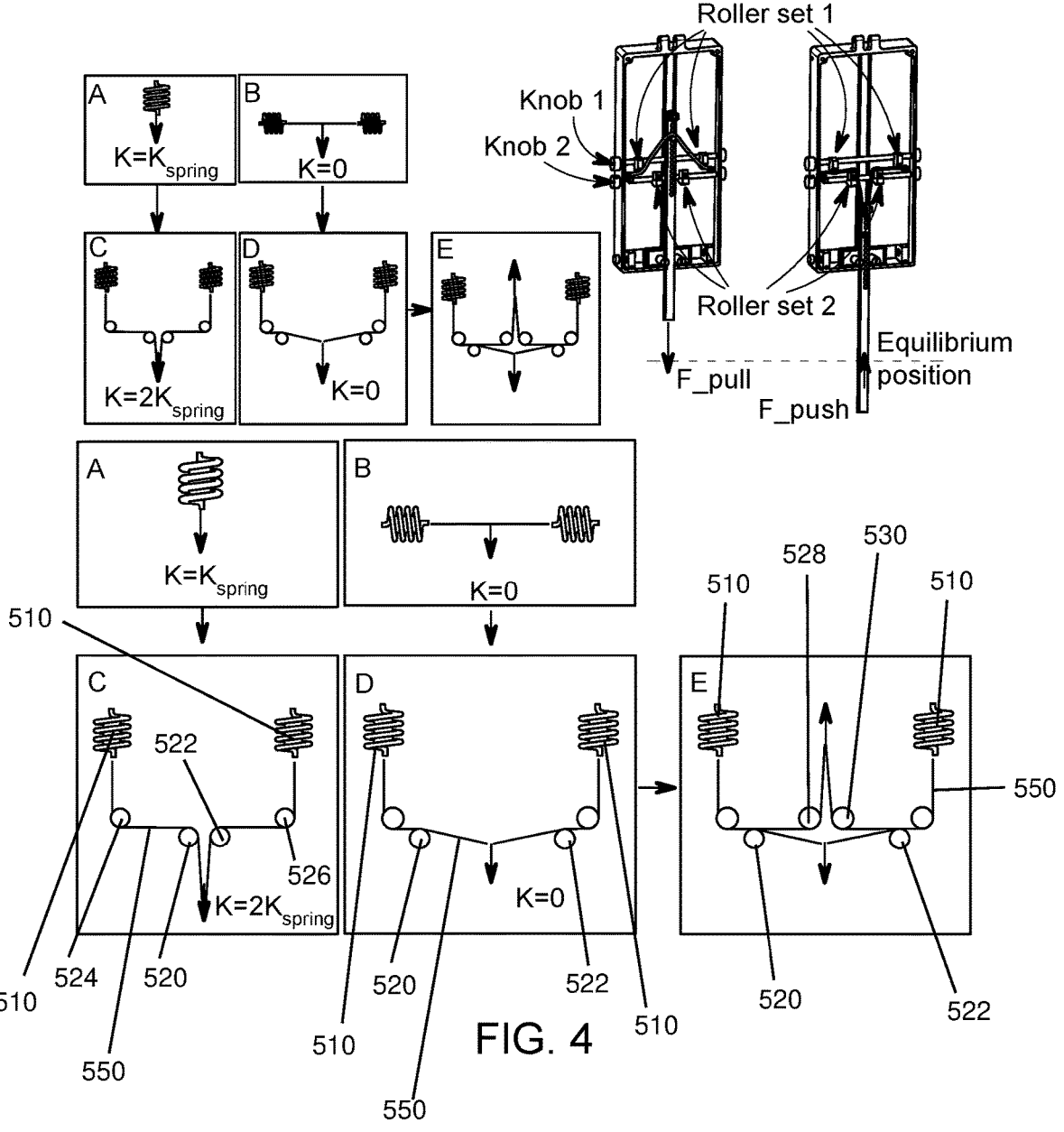
FIG. 4 depicts various arrangements of components of a variable impedance module transmission.

As described above, the variable impedance module (VIM) 400 is highly adjustable in stiffness, equilibrium position, and range of motion to fit each individual's preference and/or need through various stages of injury recovery. FIG. 4 illustrates the mechanism by which components of the VIM control stiffness. When the displacement direction is in line with the spring, the rendered stiffness K is equal to a spring stiffness $K_{spring}$ as shown in box A. When the displacement direction is perpendicular to the spring, the rendered stiffness is substantially and/or close to zero as depicted in box B.

Boxes C and D represent a variable impedance module (VIM) transmission comprising two springs 510, four rollers 520, 522, 524, 526, and a rope 550. When the two rollers 520, 522 are positioned very close to one another as shown in box C, K follows the same and/or similar relationship as that depicted in box A. In the case demonstrated in box C, $K=2K_{spring}$. When the two rollers 520, 522 are positioned further away from one another as shown in box D, K follows the same and/or similar relationship as that depicted in box B. In the case demonstrated in box D, K=0.

Box E represents a variable impedance module (VIM) transmission comprising two springs 510, six rollers 520, 522, 524, 526, 528, 530, and rope 550. Such a design allows for non-linear stiffness. With two extra rollers, 528, 530, added to the transmission from box D, the distance between the two rollers 528, 530 determines the stiffness in an upward direction. The distance between the two bottom rollers 520, 522 determines the stiffness in a downward direction. The distance between the rollers can be adjusted by knob 1 and knob 2, respectively. In various instances, the knob can be turned by a human finger and/or a motor. Roller diameter and rope angles are both key parameters that help generate theoretical profiles and directly impact ankle stiffness profiles. The VIM achieves independent stiffness when being pushed and pulled, which further determines the rotational stiffness of the mechanical support device in dorsiflexion and plantarflexion.

Figure 5:
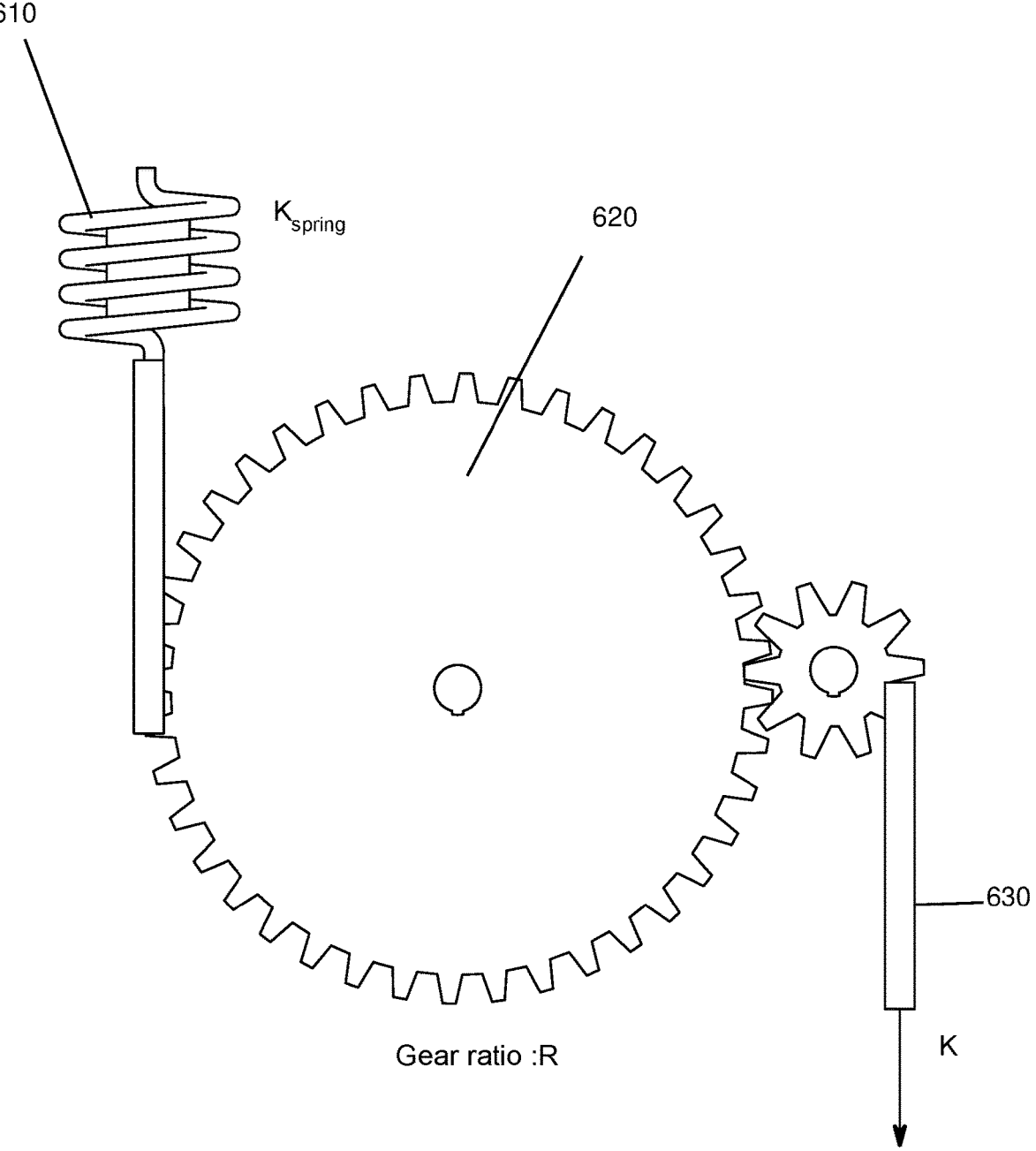
FIG. 5 depicts components of a variable impedance module for achieving adjustable stiffness.

FIG. 5 represents an embodiment for achieving adjustable stiffness in the variable impedance module (VIM). In the depicted embodiment, adjustable stiffness is achieved by adding a variable-ratio gear 620 between the spring 610, similar to springs 410, 510 and the output 630. By changing the gear ratio R, the rendered stiffness K can be changed. For example, $K=K_{spring} \times R^2$. While FIG. 5 illustrates one mechanism to achieve adjustable stiffness in a VIM, adjustable stiffness can be achieved in any suitable way.

In various instances, the mechanical support device can comprise adjustable damping. Basic damping is expressed as F=D×V, where F is force, V is speed, and D is a damping constant. Adjustable damping can be achieved in the mechanical support device by controlling the value of the damping constant. The mechanical support device can comprise a one-way damper that provides resistance in one direction and substantially zero, or a very small resistance, in the other direction.

$$F= \quad \begin{array}{l} D*V, V > 0 \\ 0, V < 0 \end{array}$$

FIG. 6 is a table depicting various specification of the mechanical support device. The mechanical support device achieves a range of motion of −30° (dorsi) to 35° (plantar). The maximum profile is 1 Nm/deg, which is determined by the coil spring. Hardstop stiffness is 11.5 Nm/deg, which is comparable to an off-the-shelf immobilization boot. The weight of an exemplary mechanical support device attached to a tennis shoe is 1.6 kg, with a tennis shoe of 0.4 kg. With 8 coil springs, the mechanical support device's highest stiffness configuration reaches 1 Nm/deg, which is enough to significantly reduce metabolic cost and/or make a significant contribution to Achilles tendon load. Achieving a higher stiffness is ideal to increase the capability and/or range of use of the variable impedance module (VIM).

Figure 7:
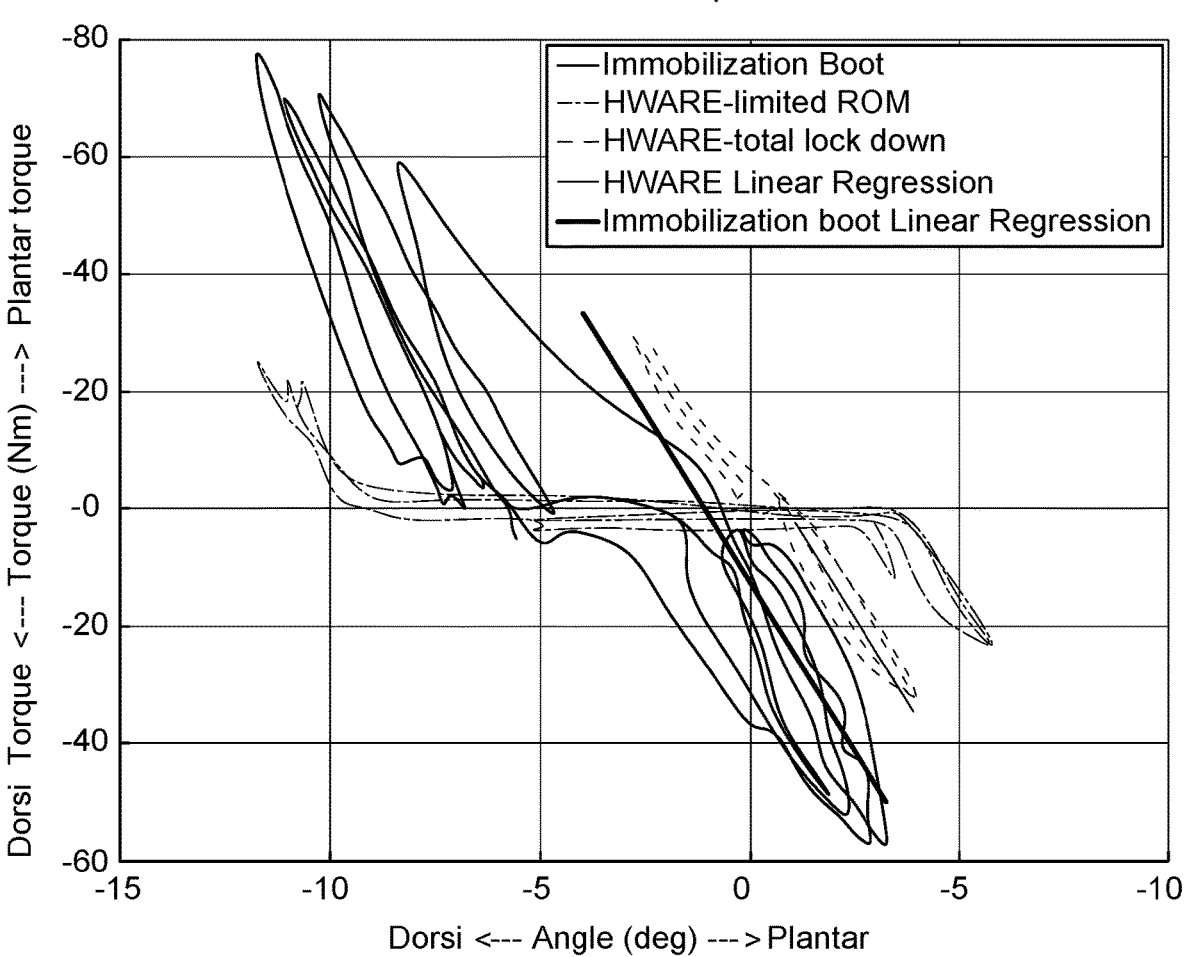
FIG. 7 illustrates a graph comparing the mechanical support device's range of motion limit adjustability against a commercial immobilization boot.

Mechanics of the support device, or exo-brace, have been characterized with a benchtop testing rig. Such mechanics were compared to the performance of a standard immobilization boot (VACOped®, Buford, GA, USA). Results of the comparison are shown in FIG. 7. The immobilization boot limited ankle joint motion with a stiffness of 11.6 Nm/deg, while the mechanical support device achieved a stiffness of 11.5 Nm/deg. Testing data for the mechanical support device is calculated using data in the plantar flexion direction in order to be consistent with immobilization boot testing. The result suggested that the mechanical support device is able to achieve similar joint locking compared to the immobilization boot.

As seen in FIG. 7, the torque-vs-angle curve of a traditional immobilization boot is plotted against a locking configuration of the mechanical support device. The locking angle is adjustable and in this configuration it was set to be 0°. Green represents a limited range of motion (ROM) where the hardstop were set to be [−9°, 3°]. The mechanical support device resists motion beyond the RoM while allowing free motion within it. Fitted linear stiffness, using linear regression, of the immobilization boot and the mechanical support device in plantarflexion direction are also displayed on the graph shown in FIG. 7. The slope of such lines are 11.6 Nm/deg and 11.5 Nm/deg, respectively. Testing data for the immobilization boot was noisy because it has some slack near the neutral angle. The max stiffness of 11.6 Nm/deg was calculated using data in the plantar flexion direction. The max stiffness data could be smaller if the entire range of data was taken into account.

The mechanical support devices disclosed herein can replace conventional rehabilitation equipment such as immobilization boots, hinged braces, compressive braces, flexibility bands, TheraBands®, and/or immobilization boards with a single, simple, and highly-adjustable device. During rehabilitation, clinicians can monitor progress using biological data to adjust the stiffness of the mechanical support device. In various instances, sensors can be embedded and/or otherwise integrated with the mechanical support device to assist with monitoring thereof. The mechanical support devices disclosed herein can comprise any combination of adjustable damping, range of motion, and/or stiffness as described in greater detail herein.

The approaches demonstrated herein could also be implemented in knee and hip exo-braces, for example, allowing researchers to explore biomechanical interactions across joints during locomotion as well as to analyze the effect of different assistance strategies.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A variable impedance module configured for use with a mechanical support device configured to support an ankle joint of a user of the mechanical support device, wherein the variable impedance module comprises:

a coil spring, wherein the variable impedance module is configured to apply a pulling force to the ankle joint when the coil spring is stretched, and wherein the variable impedance module is configured to apply a pushing force to the ankle joint when the coil spring is compressed;

a rope; and a first pair of rollers spaced a first distance apart from one another, wherein a stiffness of the ankle joint is adjustably controlled by selectively changing the first distance.

2. The variable impedance module of claim 1, further comprising a first knob, wherein the first distance is selectively controlled by rotating the first knob.

3. The variable impedance module of claim 2, wherein the first distance becomes larger by rotating the first knob in a first direction, and wherein the first distance becomes smaller by rotating the first knob in a second direction.

4. The variable impedance module of claim 1, wherein the mechanical support device comprises a passive ankle brace.

5. The variable impedance module of claim 1, wherein the stiffness is further defined by a diameter of each roller from the first pair of rollers.

6. The variable impedance module of claim 1, further comprising a second pair of rollers spaced a second distance apart from one another, wherein the stiffness of the ankle joint is adjustably controlled by selectively changing the second distance.

7. The variable impedance module of claim 6, wherein the first distance determines a downward stiffness, and wherein the second distance determines an upward stiffness.

8. The variable impedance module of claim 6, wherein the rope is routed around the second pair of rollers and is operably attached to the coil spring such that compressing the variable impedance module results in a compressive stiffness controlled by the second distance between the second pair of rollers, resulting in an amount of compression of the coil spring.

9. The variable impedance module of claim 1, wherein the rope is routed around the first pair of rollers and is operably attached to the coil spring such that elongating the variable impedance module results in the variable impedance module exhibiting a tensile stiffness controlled by the first distance between the first pair of rollers, resulting in an amount of elongation of the coil spring.

10. The variable impedance module of claim 1, further comprises a housing, wherein the coil spring is operably attached to the housing, and wherein the housing is attachable to an upper portion of the mechanical support device.

11. The variable impedance module of claim 10, further comprising a plunger movable relative to the housing, the plunger is attachable to a lower portion of the mechanical support device.

12. The variable impedance module of claim 11, wherein the rope is operably attached to the coil spring, is routed around the first pair of rollers, and is operably attached to the plunger.

13. The variable impedance module of claim 12, wherein the rope is retained between a pair of pins of the plunger to operably attach the rope to the plunger.

\* \* \* \* \*